US012597500B2

(12) United States Patent
Long

(10) Patent No.: US 12,597,500 B2
(45) Date of Patent: Apr. 7, 2026

(54) METHOD, APPARATUS FOR CONTROLLING CRYOGENIC PHYSICAL THERAPY CABIN, ELECTRONIC DEVICE AND STORAGE MEDIUM

(71) Applicant: Zhigang Long, Beijing (CN)

(72) Inventor: Zhigang Long, Beijing (CN)

( * ) Notice: Subject to any disclaimer, the term of this patent is extended or adjusted under 35 U.S.C. 154(b) by 351 days.

(21) Appl. No.: 18/449,670

(22) Filed: Aug. 14, 2023

(65) Prior Publication Data

US 2024/0055098 A1    Feb. 15, 2024

(30) Foreign Application Priority Data

Aug. 15, 2022    (CN) .......................... 202210973940.3

(51) Int. Cl.
*G06F 3/048*        (2013.01)
*G16H 20/30*        (2018.01)

(52) U.S. Cl.
CPC .................................... *G16H 20/30* (2018.01)

(58) Field of Classification Search
CPC ...................................................... G16H 20/30
See application file for complete search history.

(56) References Cited

U.S. PATENT DOCUMENTS 10,271,986 B1    4/2019  Guertin et al.
12,419,677 B2 *  9/2025  Luo ........................ A61B 18/02
(Continued)

FOREIGN PATENT DOCUMENTS

CN          203017359        6/2013
CN          108882992       11/2018
(Continued)

OTHER PUBLICATIONS

Office Action issued in corresponding Chinese Application No. 202210973940.3, dated Feb. 13, 2025 (English Translation provided).

(Continued)

*Primary Examiner* — David Phantana-angkool
(74) *Attorney, Agent, or Firm* — NORTON ROSE FULBRIGHT US LLP

(57)                ABSTRACT

The embodiments of the present invention provide a method, an apparatus for controlling a cryogenic physical therapy cabin, an electronic device and a storage medium. The method comprises: acquiring physical therapy information input by a user; acquiring target feature information of a target user, and controlling a cabin door of the physical therapy cabin to be opened when it is determined that the target feature information matches pre-stored feature information; controlling the cabin door of the physical therapy cabin to be closed after determining that the user enters the physical therapy cabin; adjusting a temperature of the physical therapy cabin to reach the physical therapy temperature, and recording the physical therapy duration of the user; and after determining that the physical therapy duration of the user reaches the physical therapy duration, adjusting the temperature of the physical therapy cabin to a preset temperature, and controlling the cabin door of the physical therapy cabin to be opened. The cryogenic physical therapy cabin can be controlled based on the physical therapy information input by the user and the target feature information of the target user, so as to complete the cryogenic physical therapy process to the user. There is no need for the assistance of staff and the cryogenic physical therapy cabin can be operated by a single user, thereby better meeting the cryogenic physical therapy needs of the user.

14 Claims, 3 Drawing Sheets

(56) References Cited

U.S. PATENT DOCUMENTS

| | | | | | |
|---|---|---|---|---|---|
| 2005/0151620 A1* | 7/2005 | Neumann | .............. | G06V 40/12 | |
| | | | | | 340/5.52 |
| 2012/0296235 A1* | 11/2012 | Rupp | .................... | G06V 40/23 | |
| | | | | | 600/595 |
| 2014/0255890 A1* | 9/2014 | Kovach | .................. | G16H 40/63 | |
| | | | | | 434/257 |
| 2015/0094702 A1* | 4/2015 | Shuppo | ................ | A61H 33/066 | |
| | | | | | 606/22 |
| 2015/0134088 A1* | 5/2015 | Romeo | .................. | G16Z 99/00 | |
| | | | | | 700/91 |
| 2017/0224527 A1 | 8/2017 | Boegelein | | | |
| 2018/0199861 A1* | 7/2018 | Ye | .......................... | G16H 20/30 | |
| 2021/0100683 A1 | 4/2021 | Brojek | | | |
| 2024/0050269 A1* | 2/2024 | Long | ......................... | A61F 7/00 | |
| 2024/0050270 A1* | 2/2024 | Long | .................. | G06Q 20/4037 | |
| 2024/0050271 A1* | 2/2024 | Long | ..................... | A61H 35/00 | |
| 2024/0055098 A1* | 2/2024 | Long | .................... | A61F 7/0053 | |
| 2025/0152955 A1* | 5/2025 | Schwarz | ................ | A61N 1/403 | |

FOREIGN PATENT DOCUMENTS

| | | |
|---|---|---|
| CN | 109568055 | 4/2019 |
| CN | 112315701 | 2/2021 |
| CN | 112353551 | 2/2021 |

OTHER PUBLICATIONS

Extended European Search Report issued in corresponding European Application No. 23191334.4, dated Jan. 3, 2024.

* cited by examiner

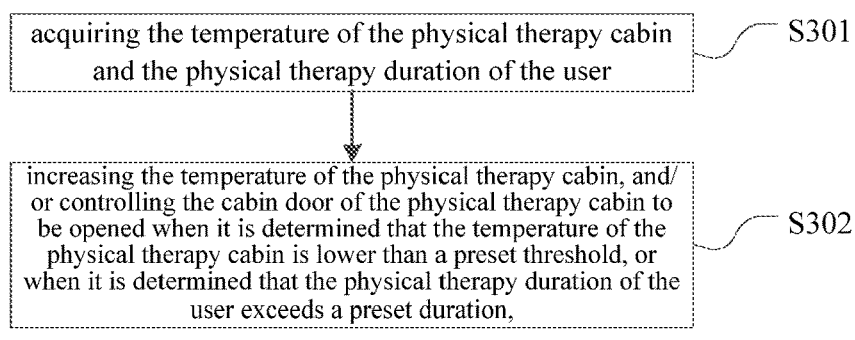

acquiring the temperature of the physical therapy cabin and the physical therapy duration of the user —— S301 increasing the temperature of the physical therapy cabin, and/or controlling the cabin door of the physical therapy cabin to be opened when it is determined that the temperature of the physical therapy cabin is lower than a preset threshold, or when it is determined that the physical therapy duration of the user exceeds a preset duration, —— S302

Fig. 3

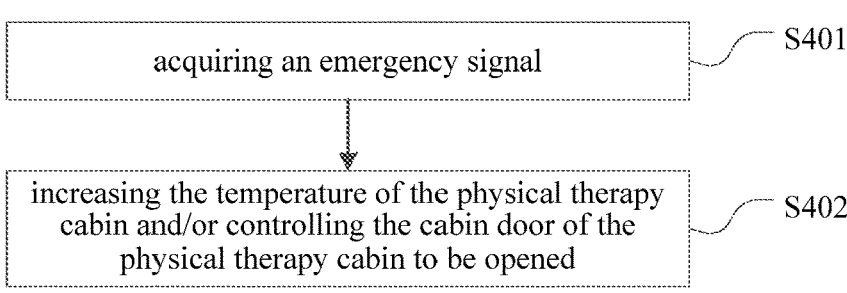

acquiring an emergency signal —— S401 increasing the temperature of the physical therapy cabin and/or controlling the cabin door of the physical therapy cabin to be opened —— S402

Fig. 4

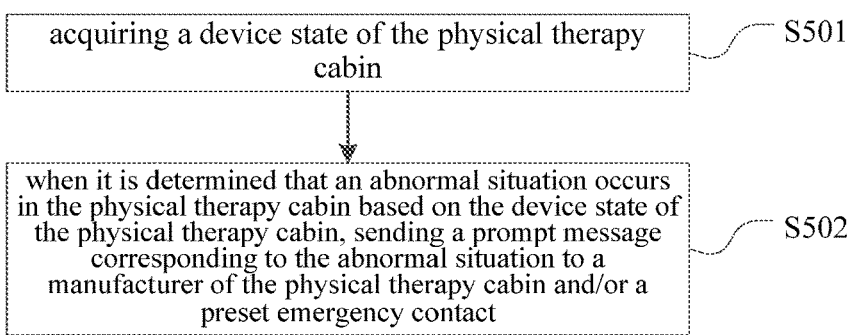

acquiring a device state of the physical therapy cabin —— S501 when it is determined that an abnormal situation occurs in the physical therapy cabin based on the device state of the physical therapy cabin, sending a prompt message corresponding to the abnormal situation to a manufacturer of the physical therapy cabin and/or a preset emergency contact —— S502

Fig. 5

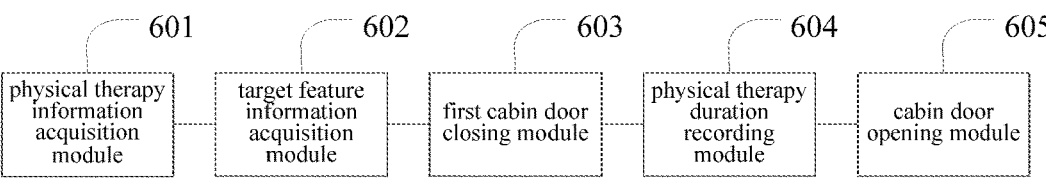

601      602      603      604      605

| physical therapy information acquisition module | target feature information acquisition module | first cabin door closing module | physical therapy duration recording module | cabin door opening module |

Fig. 6

METHOD, APPARATUS FOR CONTROLLING CRYOGENIC PHYSICAL THERAPY CABIN, ELECTRONIC DEVICE AND STORAGE MEDIUM

CROSS-REFERENCE TO RELATED APPLICATION

The present application claims the benefit of priority to Chinese Patent Application No. 202210973940.3, filed on Aug. 15, 2022, the entire contents of which are hereby incorporated by reference in their entirety.

TECHNICAL FIELD

The present invention relates to the field of cryogenic physical therapy, in particular to a method, an apparatus for controlling cryogenic physical therapy cabin, an electronic device and storage medium.

BACKGROUND

With the accelerated pace of modern life, more and more people are in sub-health state, and long-term exposure to sub health is extremely detrimental to human health. As a new physical therapy technology, cryogenic physical therapy technology is gradually entering the public eye from the traditional medical field. The cryogenic physical therapy is to keep human body in an extremely low-temperature (usually below −110° C.) environment for a period of time, such as for about 2-3 minutes. Endorphins are released from the user's body by stimulating user's skin at a low temperature, thus achieving the functional effects of accelerating blood circulation, continuously burning fat, increasing skin elasticity and eliminating muscle fatigue and so on.

A common cryogenic physical therapy device is usually controlled by specialized staff. When a user need cryogenic physical therapy, the staff can set various parameters in the process of cryogenic physical therapy in advance, such as a physical therapy duration and a physical therapy temperature and so on, then the user can enter the cryogenic physical therapy device and start to undergo the cryogenic physical therapy. Due to the low degree of intelligence of the common cryogenic physical therapy device, in the process of cryogenic physical therapy, the cryogenic physical therapy device does not support being operated by the user alone, and the cryogenic physical therapy needs the assistance from staff, so it is difficult to meet the needs of users.

SUMMARY

The purpose of the embodiment of the present invention is to provide a method, an apparatus for controlling a cryogenic physical therapy cabin, an electronic device and a storage medium to enable the cryogenic physical therapy cabin support being operated by a single user and better meet the cryogenic physical therapy needs of the user. The specific technical solution is as follows.

In a first aspect, an embodiment of the present invention provides a method for controlling a cryogenic physical therapy cabin, which comprises:

acquiring physical therapy information input by a user, wherein the physical therapy information comprises a physical therapy temperature and a physical therapy period;

acquiring target feature information of a target user, and controlling a cabin door of the physical therapy cabin to be opened when it is determined that the target feature information matches pre-stored feature information;

controlling the cabin door of the physical therapy cabin to be closed after determining that the user enters the physical therapy cabin;

adjusting a temperature of the physical therapy cabin to reach the physical therapy temperature, and recording the physical therapy duration of the user;

after determining that the physical therapy duration of the user reaches the physical therapy period, adjusting the temperature of the physical therapy cabin to a preset temperature, and controlling the cabin door of the physical therapy cabin to be opened.

Optionally, the physical therapy information further comprises a reserved physical therapy time, and a step of acquiring physical therapy information input by the user comprises:

acquiring physical therapy information input by the user through target application software, wherein the target application software is application software on an intelligent terminal pre-associated with the physical therapy cabin;

before a step of acquiring target feature information of the target user, the method further comprises:

adjusting the temperature of the physical therapy cabin to reach the physical therapy temperature after determining that a current time reaches the reserved physical therapy time.

Optionally, the physical therapy information further comprises wind speed information, and the method further comprises:

acquiring a surface temperature of four limbs and a torso of the user, or determining a surface temperature based on a current wind speed, the physical therapy temperature and a predetermined correspondence of a surface temperature, a wind speed and a temperature;

adjusting wind speeds on surfaces of the four limbs and the torso of the user based on the wind speed information and/or the surface temperature.

Optionally, after a step of adjusting the temperature of the physical therapy cabin to a preset temperature and controlling the cabin door of the physical therapy cabin to be opened, the method further comprises:

controlling the cabin door of the physical therapy cabin to be closed after determining that the user leaves the physical therapy cabin.

Optionally, the method further comprises:

acquiring a temperature of the physical therapy cabin and the physical therapy duration of the user;

increasing the temperature of the physical therapy cabin, and/or controlling the cabin door of the physical therapy cabin to be opened when it is determined that the temperature of the physical therapy cabin is lower than a preset threshold, or when it is determined that the physical therapy duration of the user exceeds a preset duration.

Optionally, the method further comprises:

acquiring an emergency signal, wherein the emergency signal is a signal generated when a preset emergency button is triggered;

increasing the temperature of the physical therapy cabin and/or controlling the cabin door of the physical therapy cabin to be opened.

Optionally, the method further comprises:

acquiring a device state of the physical therapy cabin;

when it is determined that an abnormal situation occurs in the physical therapy cabin based on the device state of the physical therapy cabin, sending a prompt message corresponding to the abnormal situation to a manufacturer of the physical therapy cabin and/or a preset emergency contact.

In a second aspect, an embodiment of the present invention provides an apparatus for controlling a cryogenic physical therapy cabin, which comprises:

a physical therapy information acquisition module, configured for acquiring physical therapy information input by a user, wherein the physical therapy information comprises a physical therapy temperature and a physical therapy period;

a target feature information acquisition module, configured for acquiring target feature information of a target user, and controlling a cabin door of the physical therapy cabin to be opened when it is determined that the target feature information matches pre-stored feature information;

a first cabin door closing module, configured for controlling the cabin door of the physical therapy cabin to be closed after determining that the user enters the physical therapy cabin;

a physical therapy duration recording module, configured for adjusting a temperature of the physical therapy cabin to reach the physical therapy temperature, and recording the physical therapy duration of the user;

a cabin door opening module, configured for, after determining that the physical therapy duration of the user reaches the physical therapy duration, adjusting the temperature of the physical therapy cabin to a preset temperature, and controlling the cabin door of the physical therapy cabin to be opened.

Optionally, the physical therapy information further comprises a reserved physical therapy time, and the physical therapy information acquisition module comprises:

a physical therapy information acquisition unit, configured for acquiring physical therapy information input by the user through target application software, wherein the target application software is application software on an intelligent terminal pre-associated with the physical therapy cabin;

the apparatus further comprises:

a reservation processing module, configured for before a step of acquiring the target feature information of the target user, adjusting the temperature of the physical therapy cabin to reach the physical therapy temperature after determining that current time reaches the reserved physical therapy time.

Optionally, the physical therapy information further comprises wind speed information, and the apparatus further comprises:

a surface temperature determination module, configured for acquiring a surface temperature of four limbs and torso of the user, or determining a surface temperature based on a current wind speed, the physical therapy temperature and a predetermined correspondence of a surface temperature, a wind speed and a temperature;

a wind speed adjusting module, configured for adjusting wind speeds of surfaces of four limbs and torso of the user based on the wind speed information and/or the surface temperature.

Optionally, the apparatus further comprises:

a second cabin door closing module, configured for, after a step of adjusting the temperature of the physical therapy cabin to the preset temperature and controlling the cabin door of the physical therapy cabin to be opened, controlling the cabin door of the physical therapy cabin to be closed after determining that the user leaves the physical therapy cabin.

Optionally, the apparatus further comprises:

a first acquisition module, configured for acquiring a temperature of the physical therapy cabin and the physical therapy duration of the user;

a first controlling module, configured for increasing the temperature of the physical therapy cabin, and/or controlling the cabin door of the physical therapy cabin to be opened when it is determined that the temperature of the physical therapy cabin is lower than a preset threshold, or when it is determined that the physical therapy duration of the user exceeds a preset duration.

Optionally, the apparatus further comprises:

a second acquisition module, configured for acquiring an emergency signal, wherein the emergency signal is a signal generated when a preset emergency button is triggered;

a second controlling module, configured for increasing the temperature of the physical therapy cabin and/or controlling the cabin door of the physical therapy cabin to be opened.

Optionally, the apparatus further comprises:

a device state acquisition module, configured for acquiring a device state of the physical therapy cabin;

a prompt message sending module, configured for, when it is determined that an abnormal situation occurs in the physical therapy cabin based on the device state of the physical therapy cabin, sending a prompt message corresponding to the abnormal situation to a manufacturer of the physical therapy cabin and/or a preset emergency contact.

In a third aspect, an embodiment of the present invention provides an electronic device, which comprises a processor, a communication interface, a memory and a communication bus, wherein the processor, the communication interface and the memory communicate with each other via the communication bus;

the memory is configured for storing a computer program;

the processor is configured for executing the program stored in the memory to implement any one of the steps described in the method as mentioned in the above first aspects.

In a fourth aspect, an embodiment of the present invention provides a computer-readable storage medium, wherein a computer program is stored in the computer-readable storage medium, which, when executed by a processor, implements any one of the steps described in the method as mentioned in the above first aspects.

The beneficial effects of the embodiments of the present invention are as follows.

In the solutions provided by the embodiment of the present invention, the electronic device can acquire physical therapy information input by a user, wherein the physical therapy information comprises a physical therapy temperature and a physical therapy period; acquire the target feature information of the target user, and controlling the cabin door of the physical therapy cabin to be opened when it is determined that the target feature information matches the pre-stored feature information. The electronic device can control the cabin door of the physical therapy cabin to be closed after determining that the user enters the physical therapy cabin; adjust a temperature of the physical therapy cabin to reach the physical therapy temperature, and record the physical therapy duration of the user; and then after determining that the physical therapy duration of the user reaches the physical therapy period, adjust the temperature of the physical therapy cabin to a preset temperature, and control the cabin door of the physical therapy cabin to be opened. The electronic device can control the cryogenic physical therapy cabin based on the physical therapy information input by the user and the target feature information of the target user, so as to complete the process of cryogenic physical therapy to the user. Since that there is no need for the assistance of staff, and the cryogenic physical therapy cabin can be operated by a single user, the cryogenic physical therapy needs of the user can be better met. Of course, it is not necessary to achieve all the advantages mentioned above at the same time to implement any product or method of the present invention.

BRIEF DESCRIPTION OF THE DRAWINGS

In order to more clearly describe the technical solutions of the embodiments of the present invention and the prior art, accompanying drawings that need to be used in the embodiments and the prior art will be briefly described below. Obviously, accompanying drawings described below are for only some of embodiments of the present invention. Those skilled in the art may also obtain other embodiments based on these accompanying drawings.

FIG. 3 is a diagram of a specific process of controlling the cryogenic physical therapy cabin based on the embodiment shown in FIG. 1;

FIG. 4 is a diagram of another specific process of controlling the cryogenic physical therapy cabin based on the embodiment shown in FIG. 1;

FIG. 5 is a diagram of a process of sending a prompt message based on the embodiment shown in FIG. 1;

FIG. 6 is a schematic diagram of a structure of an apparatus for controlling a cryogenic physical therapy cabin provided by an embodiment of the present invention;

DETAILED DESCRIPTION

In the following, the technical solutions in the embodiments of the invention will be clearly and completely described with reference to the accompanying drawings. Obviously, the described embodiments are only some, and not all, of the embodiments of the invention. All other embodiments obtained based on the embodiments of the invention by those skilled in the art fall into the scope of protection of the invention.

In order to enable the cryogenic physical therapy cabin to be operated by a single user and better meet cryogenic physical therapy needs of the user, an embodiment of the present invention provides a method and an apparatus for controlling the cryogenic physical therapy cabin, an electronic device, a computer-readable storage medium and a computer program product. The method for controlling the cryogenic physical therapy cabin provided by the embodiment of the present invention is firstly introduced below.

The method for controlling the cryogenic physical therapy cabin provided by the embodiment of the present invention can be applied to an electronic device in the cryogenic physical therapy cabin for controlling the cryogenic physical therapy process of the user. For example, the electronic device can be a programmable controller of the cryogenic physical therapy cabin, a central processing unit of a control apparatus, a server for controlling the cryogenic physical therapy cabin, etc., which is not specifically limited. For the sake of clarity, it will be referred to as the electronic device in the following.

Figure 1:
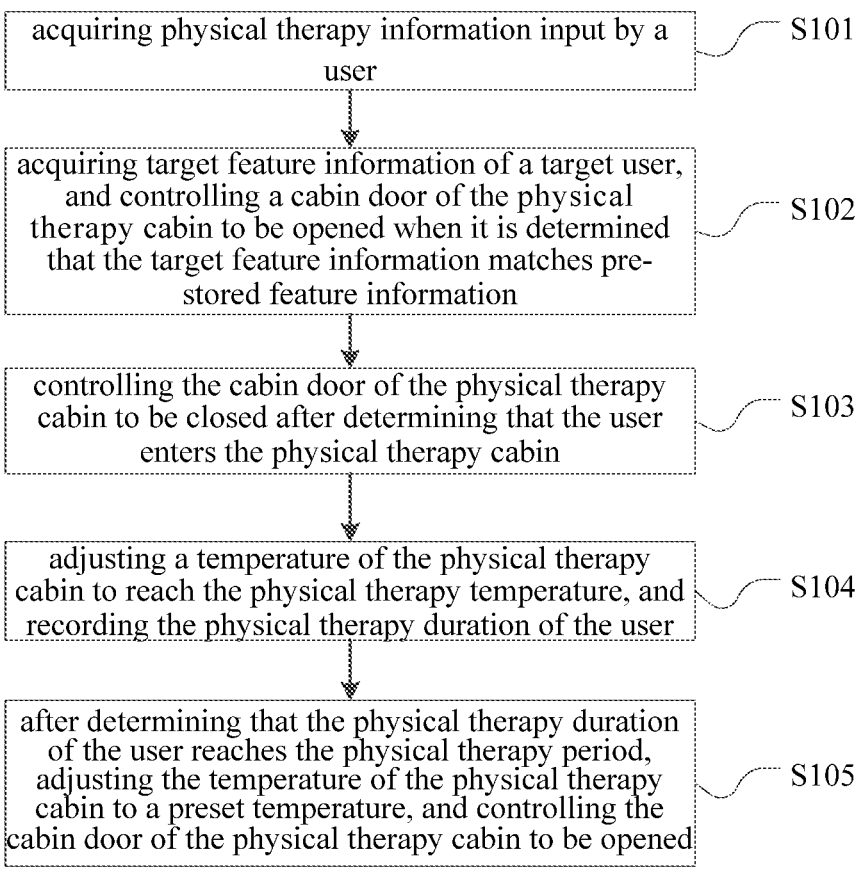
FIG. 1 is a diagram of a process of a method for controlling a cryogenic physical therapy cabin provided by an embodiment of the present invention.

As shown in FIG. 1, a method for controlling a cryogenic physical therapy cabin comprises:

S101, acquiring physical therapy information input by a user;

wherein, the physical therapy information comprises a physical therapy temperature and a physical therapy period.

S102, acquiring target feature information of a target user, and controlling a cabin door of the physical therapy cabin to be opened when it is determined that the target feature information matches pre-stored feature information.

S103, controlling the cabin door of the physical therapy cabin to be closed after determining that the user enters the physical therapy cabin.

S104, adjusting a temperature of the physical therapy cabin to reach the physical therapy temperature, and recording the physical therapy duration of the user.

S105, after determining that the physical therapy duration of the user reaches the physical therapy period, adjusting the temperature of the physical therapy cabin to a preset temperature, and controlling the cabin door of the physical therapy cabin to be opened.

It can be seen that in the solution provided by the embodiment of the present invention, the electronic device can acquire the physical therapy information input by the user, wherein the physical therapy information comprises the physical therapy temperature and the physical therapy period; acquire the target feature information of the target user, and control the cabin door of the physical therapy cabin to be opened when it is determined that the target feature information matches the pre-stored feature information. The electronic device can control the cabin door of the physical therapy cabin to be closed after determining that the user enters the physical therapy cabin; adjust a temperature of the physical therapy cabin to reach the physical therapy temperature, and record the physical therapy duration of the user; and then after determining that the physical therapy duration of the user reaches the physical therapy period, adjust the temperature of the physical therapy cabin to a preset temperature, and control the cabin door of the physical therapy cabin to be opened. The electronic device can control the cryogenic physical therapy cabin based on the physical therapy information input by the user and the target feature information of the target user acquired, so as to complete the cryogenic physical therapy process to the user. Since that there is no need for the assistance of staff and the cryogenic physical therapy cabin can be operated by a single user, the cryogenic physical therapy needs of the user can be better met.

In order to enable the cryogenic physical therapy cabin to support to be operated by a single user, in the above step S101, the electronic device can acquire the physical therapy information input by the user.

In order to enable a single user to operate the cryogenic physical therapy cabin, the user can preset physical therapy parameters for the cryogenic physical therapy before undergoing the cryogenic physical therapy. Then, after the user enters the cryogenic physical therapy cabin, the electronic device can intelligently control the process of the cryogenic physical therapy according to the physical therapy parameters preset by the user, so as to complete the process of the cryogenic physical therapy on the user. The user can input physical therapy information into the cryogenic physical therapy cabin before undergoing the cryogenic physical therapy, wherein the physical therapy information can comprise the physical therapy temperature, the physical therapy period and other information. The user can determine the corresponding physical therapy information according to his/her own physical condition and previous cryogenic physical therapy experience. For example, the physical therapy temperature can be −105° C., −110° C., −115° C., etc., and the physical therapy period can be 2 minutes, 2 minutes and 30 seconds, 3 minutes, etc., which is not specifically limited here.

The user can input the physical therapy information to the cryogenic physical therapy cabin through an operating apparatus arranged on the outer surface of the cryogenic physical therapy cabin, wherein the operating apparatus can be a touch screen supporting a touch operation, a button supporting a press operation, etc., which is not specifically limited here. In an implementation, the user can also input the physical therapy information to the cryogenic physical therapy cabin through an intelligent terminal pre-associated with the cryogenic physical therapy cabin, wherein the intelligent terminal may comprise a mobile phone, a tablet computer, an intelligent device carried by the user, etc., which is not specifically limited here. Furthermore, the electronic device can acquire the physical therapy information input by the user in the above manner.

In the above step S102, the electronic device can acquire the target feature information of the target user, and control the cabin door of the physical therapy cabin to be opened when it is determined that the target feature information matches the pre-stored feature information.

The target user may be a user who wants to use the cryogenic physical therapy cabin, including the above-mentioned user who inputs the physical therapy information. In order to verify the target user to determine whether the target user is the above-mentioned user who inputs the physical therapy information, the electronic device can acquire the target feature information of the target user.

The target feature information may comprise biometric information, which may be the facial feature information, fingerprint feature information, iris feature information of the target user etc., which is not specifically limited here. In an implementation, the target feature information can be password information input by the target user, so that the electronic device can determine whether the password information matches a password preset by the user. The pre-stored feature information can be IC (Integrated Circuit) card identification information, so that the electronic device can identify whether the IC card provided by the target user corresponds to the cryogenic physical therapy cabin; the pre-stored feature information can also be RDFI (Radio Frequency Identification) tag information, so that the electronic device can identify whether the radio frequency tag provided by the target user corresponds to the cryogenic physical therapy cabin, which is not specifically limited here.

In an implementation, when each user uses the cryogenic physical therapy cabin for the first time, the electronic device can acquire the biometric information of the user, register the biometric information and an identity of the user, and store the same in the cryogenic physical therapy cabin correspondingly. Furthermore, the cryogenic physical therapy solution corresponding to each user can be preset respectively, so that the cryogenic physical therapy needs of different users in the home can be better met.

The electronic device can determine whether the target feature information matches the pre-stored feature information, and control the cabin door of the cryogenic physical therapy cabin to be opened when it is determined that the target feature information matches the pre-stored feature information.

Furthermore, in the above step S103, the electronic device can control the cabin door of the cryogenic physical therapy cabin to be closed after determining that the user enters the cryogenic physical therapy cabin.

In the solution provided by the embodiment of the present invention, the cryogenic physical therapy cabin can be provided with a sensing device including a camera, a human body sensor and the like, and the electronic device can determine whether there is a user in the cryogenic physical therapy cabin through the sensing device, so that the electronic device can control the cabin door of the cryogenic physical therapy cabin to be closed after determining that the user enters the cryogenic physical therapy cabin.

The electronic device can adjust the temperature of the cryogenic physical therapy cabin to reach the physical therapy temperature, and record the physical therapy duration of the user, that is, execute the above step S104.

The electronic device can adjust the temperature of the cryogenic physical therapy cabin after controlling the cabin door of the cryogenic physical therapy cabin to be closed. In the solution provided by the embodiment of the present invention, the cryogenic physical therapy cabin can be provided with a refrigeration apparatus, which can reduce the temperature of the internal environment of the cryogenic physical therapy cabin, so as to provide the user with an extremely low-temperature environment required for cryogenic physical therapy. The refrigeration mode of the refrigeration apparatus can be various, for example, the refrigeration apparatus can refrigerate by using electric energy and using a compressor for charging refrigerant, and can also refrigerate through liquid nitrogen vaporization, which is not specifically limited here, as long as it can provide the extremely low-temperature environment required for cryogenic physical therapy.

The cryogenic physical therapy cabin can be provided with a temperature sensor configured for collecting the temperature data of the internal environment of the cryogenic physical therapy cabin, so that the electronic device can determine that the temperature of the cryogenic physical therapy cabin has reached the physical therapy temperature according to the temperature data collected by the temperature sensor, and then can control the refrigeration apparatus to reduce the refrigeration efficiency and maintain the temperature of the cryogenic physical therapy cabin at the physical therapy temperature. The cryogenic physical therapy cabin may also be provided with a timer to record the physical therapy duration of the user starting from the time when the temperature of the cryogenic physical therapy cabin reaches the physical therapy temperature.

Furthermore, in the above step S105, after determining that the physical therapy duration of the user reaches the physical therapy period, the electronic device can adjust the temperature of the cryogenic physical therapy cabin to a preset temperature and control the cabin door of the cryogenic physical therapy cabin to be opened.

The cryogenic physical therapy cabin can be provided with a heating apparatus, and electronic device can rapidly raise the temperature of the internal environment of the cryogenic physical therapy cabin through the heating apparatus, so that the temperature of the cryogenic physical therapy cabin can reach a preset temperature, which can be the current room temperature, so that the user can quickly get into the room temperature environment from the extremely low-temperature environment, thereby achieving the purposes of accelerating blood circulation, continuously burning fat, increasing skin elasticity and eliminating muscle fatigue.

In an implementation, in the process of cryogenic physical therapy performed by the user, the electronic device can also rapidly raise the temperature of the internal environment of the cryogenic physical therapy cabin through the heating apparatus, so as to reduce the risk of frostbite of the user during the physical therapy. Electronic device can also defrost the interior of the cryogenic physical therapy cabin through the heating apparatus, thereby improving the refrigeration efficiency of the refrigeration apparatus.

After the electronic device determines that the temperature of the cryogenic physical therapy cabin reaches the preset temperature through the temperature sensor, it can control the cabin door of the cryogenic physical therapy cabin to be opened, and the user can leave the cryogenic physical therapy cabin. Since that the temperature of the cryogenic physical therapy cabin at this time is basically the same as the room temperature, there is basically no air pressure difference between the inside and outside of the cryogenic physical therapy cabin, and the air pressure does not change drastically, so it will not pose a threat to the safety of the user. The user can also quickly adapt to the air pressure environment outside the cryogenic physical therapy cabin.

By adopting the solution provided by the embodiment of the present invention, the electronic device can acquire the physical therapy information input by the user and the target feature information of the target user, control the cabin door of the physical therapy cabin to be opened when it is determined that the target feature information matches the pre-stored feature information, control the cabin door of the physical therapy cabin to be closed after determining that the user enters the physical therapy cabin, adjust a temperature of the physical therapy cabin to reach the physical therapy temperature, and recording the physical therapy duration of the user. Then after determining that the physical therapy duration of the user reaches the physical therapy period, the electronic device can adjust the temperature of the physical therapy cabin to a preset temperature, and control the cabin door of the physical therapy cabin to be opened. This method does not need for professional staff to assist the user in the cryogenic physical therapy, therefore the cryogenic physical therapy cabin using this method can meet the needs of the user for home use. The cryogenic physical therapy cabin can be operated by a single user and the cryogenic physical therapy can be carried out at home, thus better meeting the cryogenic physical therapy needs of the user.

As an implementation of the embodiment of the present invention, the physical therapy information may also comprise reserved physical therapy time, and the above step of acquiring physical therapy information input by the user may comprise:

acquiring physical therapy information input by the user through target application software;

wherein the target application software is application software on an intelligent terminal pre-associated with the physical therapy cabin.

In order to better meet the home cryogenic physical therapy needs of the user, the user can make a reservation for the cryogenic physical therapy cabin through the target application software, that is, set the reserved physical therapy time for cryogenic physical therapy. Therefore, after the current time reaches the reserved physical therapy time, the electronic device can control the cryogenic physical therapy cabin to reduce the temperature, thereby reducing the waiting time of the user before performing cryogenic physical therapy. In this embodiment, the electronic device can pre-establish a communication connection between the user's intelligent terminal and the cryogenic physical therapy cabin, wherein a mode of the communication connection can be 4G network connection, 5G network connection, WIFI (Wireless Fidelity) connection, etc., which are not specifically limited here. Therefore, the cryogenic physical therapy cabin can be remotely controlled by the application software installed on the associated intelligent terminal. The intelligent terminal of the user can comprise a computer or a server installed with a remote client of the cryogenic physical therapy cabin, or comprise a mobile phone, a tablet computer, an intelligent device, etc. installed with the application software corresponding to the cryogenic physical therapy cabin, which is not specifically limited here.

The user can input the physical therapy information to the cryogenic physical therapy cabin through the target application software, wherein the physical therapy information can comprise the reserved physical therapy time, such that the electronic device can acquire the physical therapy information including the reserved physical therapy time.

Before the step of acquiring target feature information of the target user, the method may further comprise:

adjusting the temperature of the physical therapy cabin to reach the physical therapy temperature after determining that the current time reaches the reserved physical therapy time.

After acquiring the physical therapy information including the reserved physical therapy time, the electronic device can adjust the temperature of the cryogenic physical therapy cabin to reach the physical therapy temperature corresponding to the physical therapy information after the current time reaches the reserved physical therapy time. If the current time does not reach the reserved physical therapy time, the electronic device may not adjust the temperature of the cryogenic physical therapy cabin. For example, at 5:45 pm, on the way home from work, a user A can input physical therapy information to the cryogenic physical therapy cabin through the target application software on the mobile phone which is associated with the cryogenic physical therapy cabin at home in advance, wherein the physical therapy information may comprise a reserved physical therapy time of 6:15 pm and a physical therapy temperature of −105° C. The electronic device can adjust the temperature of the cryogenic physical therapy cabin at 6:15 until the temperature reaches −105° C. When user A gets home at 6:30, the cryogenic physical therapy cabin has been started and the temperature thereof has reached −105° C. The electronic device can acquire the biometric information of user A, and control the cabin door of the cryogenic physical therapy cabin to be opened when it is determined that the biometric information matches the pre-stored feature information of user A. After user A enters the cryogenic physical therapy cabin, the cabin door of the cryogenic physical therapy cabin can be closed, and the temperature of the cryogenic physical therapy cabin can be quickly reduced to the preset physical therapy temperature. User A does not need to wait for a long time, and can quickly undergo the cryogenic physical therapy to relieve the fatigue state in time.

It can be seen that in this embodiment, the electronic device can acquire the physical therapy information input by the user through the target application software, which can be application software on the intelligent terminal pre-associated with the cryogenic physical therapy cabin, wherein the physical therapy information can also comprise the reserved physical therapy time. Therefore, the electronic device can adjust the temperature of the physical therapy cabin to reach the physical therapy temperature after determining that the current time reaches the reserved physical therapy time, and the user can quickly start the cryogenic physical therapy. Since that the cryogenic physical therapy cabin don't have to be operated on site, the user can make a reservation for the cryogenic physical therapy cabin remotely through the application software on the intelligent terminal associated with the cryogenic physical therapy cabin. Therefore, the time for the user to wait for the cryogenic physical therapy cabin to cool down is greatly reduced, and the user can undergo cryogenic physical therapy quickly, thereby the cryogenic physical therapy needs of the user can be met more timely.

Figure 2:
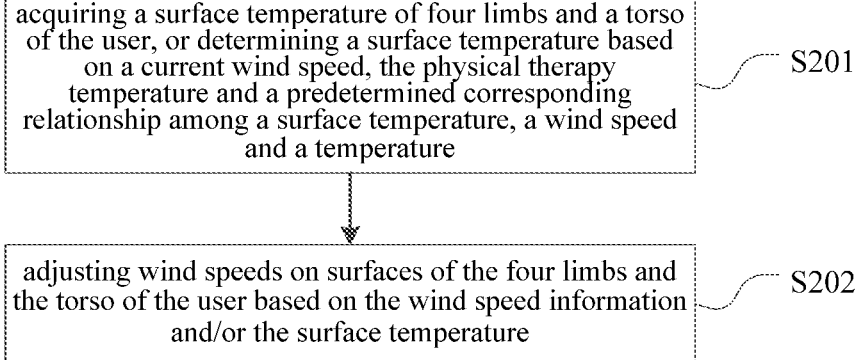
FIG. 2 is a diagram of a process of adjusting a wind speed based on the embodiment shown in FIG. 1.

As an implementation of the embodiment of the present invention, the physical therapy information may also comprise wind speed information, as shown in FIG. 2, and the method may further comprise:

S201, acquiring a surface temperature of four limbs and a torso of the user, or determining a surface temperature based on a current wind speed, a physical therapy temperature and a predetermined correspondence of a surface temperature, a wind speed and a temperature.

The physical therapy information acquired by the electronic device may also comprise wind speed information. In order to control the wind speed in the process of the cryogenic physical therapy, in this embodiment, the cryogenic physical therapy cabin may also be provided with an air vent apparatus, and the electronic device can control the air flow speed and direction in the cryogenic physical therapy cabin through the air vent apparatus. For example, when the refrigeration apparatus reduces the temperature of the cryogenic physical therapy cabin by the evaporative refrigeration of charging refrigerant with a compressor, the air vent apparatus can be connected with the evaporator to form a sealed air flow channel with an air inlet on one side and an air vent on the other side. The air vent apparatus can comprise an adjustable speed motor, fan blades and an air vent with adjustable wind direction. When the temperature in the cabin fluctuates greatly, such as when the temperature in the cabin is high, the speed of the adjustable speed fan can be increased, and otherwise, when the temperature in the cabin is low, the speed of the adjustable speed fan can be reduced, thus achieving a stable cryogenic physical therapy effect.

In the process of cryogenic physical therapy, different users have different abilities to withstand to ultra-low temperature environment because of different microcirculation in the body and different thickness of external fat. For example, some users will not feel uncomfortable in an environment of –120° C. for 3 minutes, while some users can only bear it for 2 minutes in an environment of –100° C. In one implementation, the faster the air flow speed is, the lower the apparent temperature of the user is. Therefore, when the temperature of the cryogenic physical therapy cabin is slightly high, it is not necessary to spend a lot of energy on refrigeration operation, but to increase the wind speed through the air vent apparatus to reduce the apparent temperature of the user is.

The air vent apparatus can also control the direction of air flow, so that different parts of the user's body can feel different temperatures, which can better meet the cryogenic physical therapy needs of the user since that different parts of the user's body have different sensitivities to a low temperature. The four limbs of the human body are far away from the heart, with less fat and a larger heat dissipation area compared to the torso. Therefore, under the same environmental conditions, the torso is less susceptible to cold stimulation, and the physical therapy effect thereof is not as obvious as that of the four limbs.

In order to determine an appropriate wind speed for the cryogenic physical therapy needs of different users, the electronic device acquires the wind speed information preset by users, and can also determine the surface temperature of four limbs and torso of users. In an implementation, the electronic device can acquire the surface temperature of the four limbs and torso through the temperature measuring device.

In another implementation, the faster the air flow speed is, the lower the apparent temperature of the user is. Therefore, the correspondence of the surface temperature, wind speed and temperature can be pre-established. For example, under different temperature conditions in a cryogenic physical therapy cabin, the apparent temperature of the user (unit: ° C.) corresponding to various surface wind speeds can be shown in the following table:

| surface wind speed | temperature ° C. | | | | | | | | |
|---|---|---|---|---|---|---|---|---|---|
| m/s | 4 | −4 | −12 | −20 | −40 | −60 | −80 | −100 | −120 |
| 1 | 3 | −5 | −14 | −23 | −44 | −68 | −90 | −110 | −132 |
| 2 | 2 | −7 | −17 | −26 | −49 | −74 | −96 | −120 | −143 |
| 4 | 1 | −9 | −20 | −29 | −54 | −79 | −103 | −129 | −153 |
| 7 | 0 | −11 | −22 | −31 | −57 | −83 | −108 | −134 | −159 |
| 9 | −1 | −12 | −23 | −33 | −59 | −86 | −111 | −138 | −164 |

For example, when the temperature in the cryogenic physical therapy cabin is –80° C., if the surface wind speed on the user's body surface is 2 m/s, the apparent temperature of the user is –96° C.; if the surface wind speed on the user's body surface is 7 m/s, the apparent temperature of the user is –108° C.

Therefore, the electronic device can determine the apparent temperature of the user, that is, the surface temperature of the four limbs and the torso of the user through the above table based on the current wind speed in the cryogenic physical therapy cabin and the physical therapy temperature.

S202, adjusting wind speeds on surfaces of four limbs and torso of the user based on the wind speed information and/or the surface temperature.

Therefore, the electronic device can adjust the wind speeds on the surfaces of the four limbs and torso of the user based on the acquired wind speed information preset by the user. The electronic device can also adjust the wind speeds on the surfaces based on the surface temperature of the for limbs and torso of the user. The electronic device can also adjust the wind speeds on the surfaces of the four limbs and torso of the user based on the wind speed information and the surface temperature. For example, the wind speed information preset by the user is a low wind speed, and the surface temperature of the torso of the user acquired by the electronic device is high. If the wind speed is not adjusted, the physical therapy effect on the torso of the user may be poor. In order to achieve a better physical therapy effect of cryogenic physical therapy, the electronic device can control the air vent apparatus to aim the air outlet with adjustable wind direction at the torso of the user, and increase the speed of the adjustable speed fan. In this way, the torso which is not easily stimulated by cold can achieve a better physical therapy effect.

It can be seen that in this embodiment, the electronic device can acquire the surface temperature of the four limbs and torso of the user, or determine the surface temperature based on the current wind speed, the physical therapy temperature and the predetermined correspondence of the surface temperature, the wind speed and the temperature, and adjust the wind speeds on the surfaces of the four limbs and torso of the user based on the wind speed information preset by the user and/or the surface temperature of the four limbs and torso of the user. Based on the above solution, each of different body parts of the user can achieve a better physical therapy effect by adjusting the wind speed, although different body parts of the user have different sensitivity to extremely low-temperature environment; the cryogenic physical therapy needs of different users can also be better met by adjusting the wind speed to change the apparent temperature of the user. And by increasing the wind speed, the user can feel a lower apparent temperature without reducing the physical therapy temperature, thus reducing the energy consumption of the cryogenic physical therapy.

As an implementation of the embodiment of the present invention, after the step of adjusting the temperature of the physical therapy cabin to a preset temperature and controlling the cabin door of the physical therapy cabin to be opened, the method may further comprise:

controlling the cabin door of the physical therapy cabin to be closed after determining that the user leaves the physical therapy cabin.

The cryogenic physical therapy cabin is provided with a sensing device such as a camera, a human body sensor, thus the electronic device can determine whether there is a user in the cryogenic physical therapy cabin through the sensing device. After the electronic device adjusts the temperature of the cryogenic physical therapy cabin to a preset temperature and controls the cabin door of the cryogenic physical therapy cabin to be opened, the electronic device determines that the user leaves the cryogenic physical therapy cabin through the sensing device, and then can control the cabin door of the cryogenic physical therapy cabin to be closed. This avoids danger caused by a stranger or a child etc. accidentally entering the cryogenic physical therapy cabin.

In an implementation, after the user completes the cryogenic physical therapy and leaves the cryogenic physical therapy cabin, the electronic device can also control the heating apparatus to perform a heating operation. For example, when the electronic device senses, through the temperature sensor of the sensing device, that the temperature of the evaporator was low but the internal environment of the cryogenic physical therapy cabin cooled slowly in the last process of cryogenic physical therapy, it can control the heating device to heat the evaporator to remove the frost on the surface of the evaporator, so as to improve the cooling efficiency.

It can be seen that in this embodiment, after adjusting the temperature of the cryogenic physical therapy cabin to a preset temperature and controlling the cabin door of the cryogenic physical therapy cabin to be opened, the electronic device can control the cabin door of the cryogenic physical therapy cabin to be closed after determining that the user leaves the cryogenic physical therapy cabin. This prevents a stranger from entering the cryogenic physical therapy cabin. When the cryogenic physical therapy cabin is placed in a home for use, the cabin door is closed to prevent a child from accidentally entering the cryogenic physical therapy cabin, thereby reducing the risk of low-temperature frostbite that may be caused by other people accidentally entering the cryogenic physical therapy cabin.

As an implementation of the embodiment of the present invention, as shown in FIG. 3, the method may further comprise:

S301, acquiring a temperature of the physical therapy cabin and the physical therapy duration of the user.

In the process of the cryogenic physical therapy of the user, if the internal temperature of the cryogenic physical therapy cabin is too low or the duration of cryogenic physical therapy is too long, it may be difficult for the user to notice during the physical therapy, but the prolonged ultra-low temperature environment may bring harm to user's body. In addition, the cryogenic physical therapy cabin may fail, which may lead to abnormal operation of the refrigeration apparatus and the air vent apparatus, etc., and cause the risk of frostbite to the user. In order to reduce the risk of frostbite to the user in the process of cryogenic physical therapy, the electronic device can acquire the temperature of the cryogenic physical therapy cabin through the temperature sensor and the physical therapy duration of the user through the timer.

S302, increasing the temperature of the physical therapy cabin, and/or controlling the cabin door of the physical therapy cabin to be opened when it is determined that the temperature of the physical therapy cabin is lower than a preset threshold, or when it is determined that the physical therapy duration of the user exceeds a preset duration.

The electronic device can compare the acquired temperature of the cryogenic physical therapy cabin with the preset temperature threshold, and compare the physical therapy duration of the user with the preset duration. The preset threshold and preset duration can be set based on the experience of different users. For example, the preset threshold can be −125° C., −130° C., etc., and the preset duration can be 3 minutes and 30 seconds, 4 minutes, etc., which are not specifically limited here.

When the temperature of the cryogenic physical therapy cabin is lower than the preset threshold, or the physical therapy duration of the user exceeds the preset duration, the user may be at a risk of frostbite if he/she continues the cryogenic physical therapy. Therefore, the electronic device can control the heating apparatus to increase the temperature of the cryogenic physical therapy cabin; electronic device can also control the cabin door of the cryogenic physical therapy cabin to be opened; the electronic device can also both increase the temperature of the cryogenic physical therapy cabin and control the cabin door of the cryogenic physical therapy cabin to be opened, which enables the user quickly leave the extremely low-temperature environment, and avoid being frostbitten by extremely low temperature.

It can be seen that in this embodiment, the electronic device can acquire the temperature of the physical therapy cabin and the physical therapy duration of the user, and when it is determined that the temperature of the physical therapy cabin is lower than the preset threshold, or when it is determined that the physical therapy duration of the user exceeds the preset duration, control the heating apparatus to increase the temperature of the physical therapy cabin, or control the cabin door of the physical therapy cabin to be opened, or both control the heating apparatus to increase the temperature of the physical therapy cabin and control the cabin door of the physical therapy cabin to be opened. It enables the user quickly leave the extremely low-temperature environment when being used by a single person, and the risk that the user is frostbitten by the extremely low temperature is reduced.

As an implementation of the embodiment of the present invention, as shown in FIG. 4, the above method may further comprise:

S401, acquiring an emergency signal;

wherein the emergency signal is a signal generated when a preset emergency button is triggered.

In order to further improve the safety of the user in cryogenic physical therapy and reduce the risk that the user is frostbitten, in the solution provided by the embodiment of the present invention, the cryogenic physical therapy cabin can also comprise an emergency button, which can be arranged inside or outside the cryogenic physical therapy cabin or be arranged both inside and outside the cryogenic physical therapy cabin. When the emergency button is triggered, an emergency signal can be generated, which indicates that the user may have a security risk. The electronic device can acquire the emergency signal.

In an implementation, the emergency button is arranged inside the cryogenic physical therapy cabin. When the user feels uncomfortable in the process of cryogenic physical therapy, he/she can press the emergency button arranged inside the cryogenic physical therapy cabin, and the electronic device can acquire the emergency signal generated when the emergency button is triggered.

In another implementation, the emergency button can be arranged outside the cryogenic physical therapy cabin. In the process of cryogenic physical therapy of the user, other family members can observe the situation inside the cryogenic physical therapy cabin, for example, through the transparent glass observation window on the cabin door, or acquire a monitoring video during the physical therapy of the user in real time via a camera arranged inside the cryogenic physical therapy cabin. If other family members determine that the user may be uncomfortable, or the physical therapy duration of the user exceeds the preset duration, they can press the emergency button arranged outside the cryogenic physical therapy cabin, and the electronic device can acquire the emergency signal generated when the emergency button is triggered.

In yet another implementation, the cryogenic physical therapy cabin may comprise a plurality of emergency buttons, which are respectively arranged inside and outside the cryogenic physical therapy cabin. Therefore, in the process of cryogenic physical therapy, both the user and his/her family members can press the emergency button when it is determined that the user may be in danger, and the electronic device can acquire the emergency signal generated when the emergency button is triggered.

S402, increasing the temperature of the physical therapy cabin and/or controlling the cabin door of the physical therapy cabin to be opened.

After the electronic device acquires the emergency signal, it can be determined that the user may have a safety risk, thus the electronic device can control the heating apparatus to increase the temperature of the cryogenic physical therapy cabin; electronic device can also control the cabin door of the cryogenic physical therapy cabin to be opened; the electronic device can also both increase the temperature of the cryogenic physical therapy cabin and control the cabin door of the cryogenic physical therapy cabin to be opened, which enables the user quickly leave the extremely low-temperature environment, and avoid being frostbitten by the extremely low temperature, and further improves the safety of the process of the cryogenic physical therapy.

It can be seen that in this embodiment, the electronic device can acquire the emergency signal generated when the preset emergency button is triggered, and determine that the user may have a safety risk based on the emergency signal, and then control the heating apparatus to increase the temperature of the physical therapy cabin, or control the cabin door of the physical therapy cabin to be opened, or both control the heating apparatus to increase the temperature of the physical therapy cabin and control the cabin door of the physical therapy cabin to be opened. Whether the cryogenic physical therapy cabin is used by a single user or used under the observation of family members, the user can quickly leave the extremely low-temperature environment, which reduces the probability of a safety risk for the user and improves the safety of the process of the cryogenic physical therapy.

As an implementation of the embodiment of the present invention, as shown in FIG. 5, the method may further comprise:

S501: acquiring the device state of the physical therapy cabin.

In the solution provided by the embodiment of the present invention, the electronic device can acquire the device state information of the cryogenic physical therapy cabin, wherein the device state information can be used for determining whether an abnormal situation occurs in the cryogenic physical therapy cabin. The device state information may comprise the sensing data of the internal environment of the cryogenic physical therapy cabin acquired by the sensing device, such as temperature data, humidity data, human body data, monitoring video, physical therapy duration and other data; the device state information may also comprise the device information of the cryogenic physical therapy cabin, such as the location information, device usage times, device failure information and other information of the cryogenic physical therapy cabin, which is not specifically limited here.

S502: when it is determined that an abnormal situation occurs in the physical therapy cabin based on the device state of the physical therapy cabin, sending a prompt message corresponding to the abnormal situation to a manufacturer of the physical therapy cabin and/or a preset emergency contact.

The electronic device can determine whether an abnormal situation occurs in the cryogenic physical therapy cabin based on the device state of the cryogenic physical therapy cabin, and when it is determined that an abnormal situation occurs in the cryogenic physical therapy cabin, send a prompt message corresponding to the abnormal situation to the manufacturer of the cryogenic physical therapy cabin and/or a preset emergency contact.

In an implementation, a communication connection between the alarm device of the manufacturer of the cryogenic physical therapy cabin and the cryogenic physical therapy cabin can be pre-established, or a communication connection between the intelligent terminal of the emergency contact and the cryogenic physical therapy cabin can be established. The mode of the communication connection can comprise 4G network connection, 5G network connection, WIFI connection, etc., which are not specifically limited here.

Therefore, when the electronic device determines that an abnormal situation occurs in the cryogenic physical therapy cabin based on the device state of the cryogenic physical therapy cabin, the type of the abnormal situation can be determined. For example, when the abnormal situation is that the circuit has a fault and the cabin door cannot be opened, the electronic device can generate a corresponding prompt message based on the abnormal situation, and the prompt message can correspondingly be "the circuit of the cryogenic physical therapy cabin a set in area A has a fault and the cabin door cannot be opened". The electronic device can send the prompt message to the alarm device of the manufacturer which is in communication connection with the cryogenic physical therapy cabin, so that the manufacturer can determine the location of the cryogenic physical therapy cabin where the abnormal situation has occurred based on the acquired prompt message and arrange the staff for maintenance.

For another example, when the abnormal situation is that the physical therapy duration of the user in the cryogenic physical therapy cabin is too long, the electronic device can generate a prompt message of "the physical therapy duration of the user in the cryogenic physical therapy cabin b set in area B is too long, please deal with it as soon as possible". The electronic device can send the prompt message to the alarm device of the manufacturer and send the prompt message to the intelligent terminal of the preset emergency contact. The electronic device can also acquire the monitoring video in the cryogenic physical therapy cabin through the camera set in the cabin, and send the monitoring video to the alarm device of the manufacturer and the intelligent terminal of the emergency contact. Therefore, the staff of the manufacturer can determine whether the user has a safety risk, and remotely force the cryogenic physical therapy cabin to be closed, and the staff of the manufacturer and the emergency contact can also quickly check the physical condition of the user and carry out emergency rescue.

It can be seen that, in this embodiment, the electronic device can acquire the device state of the cryogenic physical therapy cabin, and when it is determined that an abnormal situation occurs in the cryogenic physical therapy cabin based on the device state of the cryogenic physical therapy cabin, send a prompt message corresponding to the abnormal situation to a manufacturer of the cryogenic physical therapy cabin; the electronic device can also send the prompt message corresponding to the abnormal situation to a preset emergency contact. Therefore, when the cryogenic physical therapy cabin needs maintenance, the manufacturer can be automatically notified for maintenance, and when the user is in danger, the emergency contact and the manufacturer can be notified in order to quickly remove the danger and provide emergency rescue to the user, thereby improving the safety of cryogenic physical therapy.

Corresponding to the above method for controlling the cryogenic physical therapy cabin, the embodiment of the present invention also provides an apparatus for controlling the cryogenic physical therapy cabin. The apparatus for controlling the cryogenic physical therapy cabin provided by the embodiment of the present invention will be introduced below.

As shown in FIG. 6, an apparatus for controlling a cryogenic physical therapy cabin comprises:

a physical therapy information acquisition module 601, configured for acquiring physical therapy information input by a user, wherein the physical therapy information comprises a physical therapy temperature and a physical therapy period;

a target feature information acquisition module 602, configured for acquiring target feature information of a target user, and controlling a cabin door of the physical therapy cabin to be opened when it is determined that the target feature information matches pre-stored feature information;

a first cabin door closing module 603, configured for controlling the cabin door of the physical therapy cabin to be closed after determining that the user enters the physical therapy cabin;

a physical therapy duration recording module 604, configured for adjusting a temperature of the physical therapy cabin to reach the physical therapy temperature, and recording the physical therapy duration of the user;

a cabin door opening module 605, configured for, after determining that the physical therapy duration of the user reaches the physical therapy duration, adjusting the temperature of the physical therapy cabin to a preset temperature, and controlling the cabin door of the physical therapy cabin to be opened.

It can be seen that in the solution provided by the embodiment of the present invention, the electronic device can acquire the physical therapy information input by the user, wherein the physical therapy information comprises the physical therapy temperature and the physical therapy period; acquire the target feature information of the target user, and control the cabin door of the physical therapy cabin to be opened when it is determined that the target feature information matches the pre-stored feature information. The electronic device can control the cabin door of the physical therapy cabin to be closed after determining that the user enters the physical therapy cabin; adjust the temperature of the physical therapy cabin to reach the physical therapy temperature, and record the physical therapy duration of the user; and then after determining that the physical therapy duration of the user reaches the physical therapy period, adjust the temperature of the physical therapy cabin to the preset temperature, and control the cabin door of the physical therapy cabin to be opened. The electronic device can control the cryogenic physical therapy cabin based on the physical therapy information input by the user and the target feature information of the target user, so as to complete the cryogenic physical therapy process of the user. Since that there is no need for the assistance of staff and the cryogenic physical therapy cabin can be operated by a single user, the cryogenic physical therapy needs of the user can be better met.

As an implementation of the embodiment of the present invention, the physical therapy information may further comprise reserved physical therapy time, and the physical therapy information acquisition module 601 may comprise:

a physical therapy information acquisition unit, configured for acquiring physical therapy information input by the user through target application software;

wherein the target application software is application software on an intelligent terminal pre-associated with the physical therapy cabin.

The apparatus may further comprise:

a reservation processing module, configured for before the step of acquiring the target feature information of the target user, adjusting the temperature of the physical therapy cabin to reach the physical therapy temperature after determining that current time reaches the reserved physical therapy time.

As an implementation of the embodiment of the present invention, the physical therapy information may further comprise wind speed information, and the apparatus may further comprise:

a surface temperature determination module, configured for acquiring a surface temperature of four limbs and torso of the user, or determining a surface temperature based on a current wind speed, and a predetermined correspondence of a wind speed and a temperature;

a wind speed adjusting module, configured for adjusting wind speeds on surfaces of four limbs and torso of the user based on the wind speed information and the surface temperatures.

Figure 7:
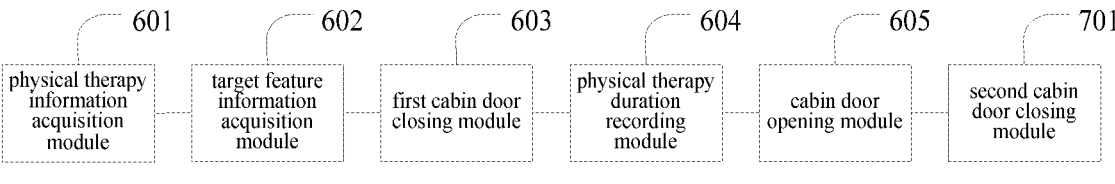
FIG. 7 is a schematic diagram of another structure of an apparatus for controlling a cryogenic physical therapy cabin provided by an embodiment of the present invention.

As an implementation of the embodiment of the present invention, as shown in FIG. 7, the apparatus may further comprise:

a second cabin door closing module 701, configured for, after the step of adjusting the temperature of the physical therapy cabin to the preset temperature and controlling the cabin door of the physical therapy cabin to be opened, controlling the cabin door of the physical therapy cabin to be closed after determining that the user leaves the physical therapy cabin.

As an implementation of the embodiment of the present invention, the apparatus may further comprise:

a first acquisition module, configured for acquiring a temperature of the physical therapy cabin and the physical therapy duration of the user;

a first controlling module, configured for increasing the temperature of the physical therapy cabin, and/or controlling the cabin door of the physical therapy cabin to be opened when it is determined that the temperature of the physical therapy cabin is lower than a preset threshold, or when it is determined that the physical therapy duration of the user exceeds a preset duration.

As an implementation of the embodiment of the present invention, the apparatus may further comprise:

a second acquisition module, configured for acquiring an emergency signal, wherein the emergency signal is a signal generated when a preset emergency button is triggered;

a second controlling module, configured for increasing the temperature of the physical therapy cabin and/or controlling the cabin door of the physical therapy cabin to be opened.

As an implementation of the embodiment of the present invention, the apparatus may further comprise:

a device state acquisition module, configured for acquiring the device state of the physical therapy cabin;

a prompt message sending module, configured for, when it is determined that an abnormal situation occurs in the physical therapy cabin based on the device state of the physical therapy cabin, sending a prompt message corresponding to the abnormal situation to a manufacturer of the physical therapy cabin and/or a preset emergency contact.

Figure 8:
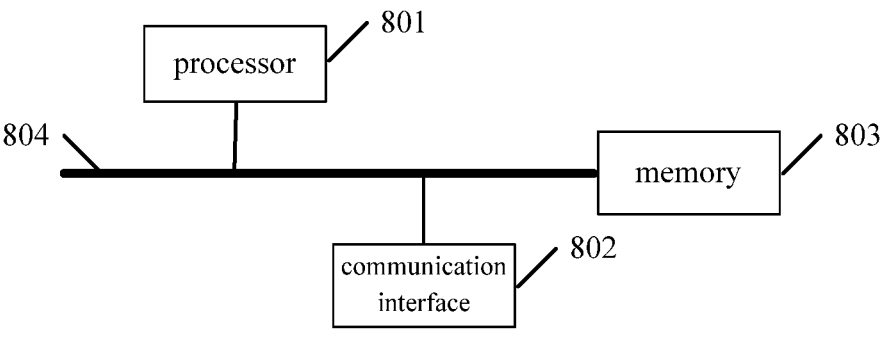
FIG. 8 is a schematic diagram of a structure of an electronic device provided by an embodiment of the present invention.

An embodiment of the present invention also provides an electronic device, as shown in FIG. 8, which comprises a processor 801, a communication interface 802, a memory 803 and a communication bus 804, wherein the processor 801, the communication interface 802 and the memory 803 communicate with each other via the communication bus 804, the memory 803 is configured for storing a computer program;

the processor 801 is configured for executing the program stored in the memory 803 to implement the method steps described in any of the above embodiments.

The communication bus mentioned in the electronic device can be a peripheral Component Interconnect (PCI) bus or an Extended Industry Standard Architecture (EISA) bus. The communication bus can be divided into address bus, data bus and control bus. For ease of representation, it is only represented by a thick line in the figure, but it does not mean that there is only one bus or one type of bus.

The communication interface is configured for communication between the electronic device and other equipment.

The memory may comprise Random Access Memory (RAM) or Non-Volatile Memory (NVM), such as at least one disk memory. Optionally, the memory can also be at least one storage device located far away from the aforementioned processor.

The processor can be a general processor, including a Central Processing Unit (CPU) and a Network Processor (NP). It can also be a Digital Signal Processor (DSP), an Application Specific Integrated Circuit (ASIC), a Field-Programmable Gate Array (FPGA) or other programmable logic devices, discrete gate or transistor logic devices, and discrete hardware components.

In another embodiment provided by the present invention, a computer-readable storage medium is also provided, wherein a computer program is stored, and the computer program, when executed by a processor, realizes the steps of the method described in any of the above embodiments.

In yet another embodiment provided by the present invention, a computer program product containing instructions is also provided, which, when runs on a computer, causes the computer to perform the method steps described in any of the above embodiments.

The above embodiments can be implemented in whole or in part by software, hardware, firmware or any combination thereof. When implemented using software, it can be fully or partially implemented in the form of a computer program product. The computer program product comprises one or more computer instructions. When the computer program instructions are loaded and executed on a computer, the processes or functions according to the embodiments of the present invention are generated in whole or in part. The computer can be a general-purpose computer, a special-purpose computer, a computer network, or other programmable devices. The computer instructions can be stored in a computer-readable storage medium or transmitted from one computer-readable storage medium to another. For example, the computer instructions can be transmitted from one website, computer, server or data center to another website, computer, server or data center by wired (such as coaxial cable, optical fiber, digital subscriber line (DSL)) or wireless (such as infrared, wireless, microwave, etc.). The computer-readable storage medium can be any available medium that a computer can access or a data storage device such as a server, a data center and the like that contains one or more available media integration. The available medium may be a magnetic medium (e.g., floppy disk, hard disk, magnetic tape), an optical medium (e.g., DVD), or a semiconductor medium (e.g., Solid State Disk (SSD)) and the like.

It should be noted that in this paper, relational terms such as first and second are only used to distinguish one entity or operation from another entity or operation, and do not necessarily require or imply that there is any such actual relationship or order between these entities or operations. Moreover, the terms "including", "comprising" or any other variation thereof are intended to cover non-exclusive inclusion, so that a process, method, article or equipment including a series of elements comprises not only those elements, but also other elements that are not explicitly listed or elements inherent to such process, method, article or equipment. Without further restrictions, an element defined by the statement "including one" does not exclude the existence of other identical elements in the process, method, article or equipment including the element.

Each embodiment in this specification is described in a relevant manner, and only the same and similar parts between the embodiments can be referred to each other, and each embodiment focuses on the differences from other embodiments. Especially, for embodiments of the device, electronic device, computer-readable storage medium and computer program product, since it is basically similar to the method embodiment, the description thereof is relatively simple. Please refer to the partial explanation of method embodiments for relevant details.

The above is only the preferred embodiment of the present invention, and is not intended to limit the scope of protection of the present invention. Any modification, equivalent substitution, improvement, etc. made within the spirit and principle of the present invention are comprised within the protection scope of the present invention.

What is claimed is:

1. A method for controlling a cryogenic physical therapy cabin, comprising:

acquiring physical therapy information input by a user, wherein the physical therapy information comprises a physical therapy temperature and a physical therapy period, wherein the physical therapy information further comprises wind speed information;

acquiring target feature information of a target user, and controlling a cabin door of the cryogenic physical therapy cabin to be opened when it is determined that the target feature information matches pre-stored feature information;

controlling the cabin door of the cryogenic physical therapy cabin to be closed after determining that the user enters the cryogenic physical therapy cabin through a sensing device of the cryogenic physical therapy cabin;

adjusting a temperature of the cryogenic physical therapy cabin to reach the physical therapy temperature, and recording a physical therapy duration of the user;

after determining that the physical therapy duration of the user reaches the physical therapy period, adjusting the temperature of the cryogenic physical therapy cabin to a preset temperature through a heating apparatus of the cryogenic physical therapy cabin, and controlling the cabin door of the cryogenic physical therapy cabin to be opened;

acquiring a surface temperature of four limbs and a torso of the user, or determining a surface temperature based on a current wind speed, the physical therapy temperature and a predetermined correspondence of a surface temperature, a wind speed and a temperature; and adjusting wind speeds on surfaces of the four limbs and the torso of the user through an air vent apparatus of the cryogenic physical therapy cabin based on the wind speed information and/or the surface temperature.

2. The method according to claim 1, wherein the physical therapy information further comprises a reserved physical therapy time, and acquiring physical therapy information input by a user, comprises:

acquiring the physical therapy information input by the user through target application software, wherein the target application software is application software on an intelligent terminal pre-associated with the cryogenic physical therapy cabin; before acquiring target feature information of a target user, the method further comprises:

adjusting the temperature of the cryogenic physical therapy cabin to reach the physical therapy temperature after determining that a current time reaches the reserved physical therapy time.

3. The method according to claim 1, wherein after adjusting the temperature of the cryogenic physical therapy cabin to a preset temperature, and controlling the cabin door of the cryogenic physical therapy cabin to be opened, the method further comprises:

controlling the cabin door of the cryogenic physical therapy cabin to be closed after determining that the user leaves the cryogenic physical therapy cabin.

4. The method according to claim 1, wherein the method further comprises:

acquiring the temperature of the cryogenic physical therapy cabin and the physical therapy duration of the user;

increasing the temperature of the cryogenic physical therapy cabin, and/or controlling the cabin door of the cryogenic physical therapy cabin to be opened when it is determined that the temperature of the cryogenic physical therapy cabin is lower than a preset threshold, or when it is determined that the physical therapy duration of the user exceeds a preset duration.

5. The method according to claim 1, wherein the method further comprises:

acquiring an emergency signal, wherein the emergency signal is a signal generated when a preset emergency button is triggered;

increasing the temperature of the cryogenic physical therapy cabin and/or controlling the cabin door of the cryogenic physical therapy cabin to be opened.

6. The method according to claim 1, wherein the method further comprises:

acquiring a device state of the cryogenic physical therapy cabin;

when it is determined that an abnormal situation occurs in the cryogenic physical therapy cabin based on the device state of the cryogenic physical therapy cabin, sending a prompt message corresponding to the abnormal situation to a manufacturer of the cryogenic physical therapy cabin and/or a preset emergency contact.

7. An apparatus for a cryogenic physical therapy cabin, comprising:

a physical therapy information acquisition module, configured for acquiring physical therapy information input by a user, wherein the physical therapy information comprises a physical therapy temperature and a physical therapy period, wherein the physical therapy information further comprises wind speed information;

a target feature information acquisition module, configured for acquiring target feature information of a target user, and controlling a cabin door of the cryogenic physical therapy cabin to be opened when it is determined that the target feature information matches pre-stored feature information;

a first cabin door closing module, configured for controlling the cabin door of the cryogenic physical therapy cabin to be closed after determining that the user enters the cryogenic physical therapy cabin through a sensing device of the cryogenic physical therapy cabin;

a physical therapy duration recording module, configured for adjusting a temperature of the cryogenic physical therapy cabin to reach the physical therapy temperature, and recording a physical therapy duration of the user;

a cabin door opening module, configured for after determining that the physical therapy duration of the user reaches the physical therapy duration, adjusting the temperature of the cryogenic physical therapy cabin to a preset temperature through a heating apparatus of the cryogenic physical therapy cabin, and controlling the cabin door of the cryogenic physical therapy cabin to be opened;

a surface temperature determination module, configured for acquiring a surface temperature of four limbs and a torso of the user, or determining a surface temperature based on a current wind speed, the physical therapy temperature and a predetermined correspondence of a surface temperature, a wind speed and a temperature; and a wind speed adjusting module, configured for adjusting wind speeds on surfaces of the four limbs and the torso of the user through an air vent apparatus of the cryogenic physical therapy cabin based on the wind speed information and/or the surface temperature.

8. The apparatus according to claim 7, wherein the physical therapy information further comprises a reserved physical therapy time, and the physical therapy information acquisition module comprises:

a physical therapy information acquisition unit, configured for acquiring the physical therapy information input by the user through target application software, wherein the target application software is application software on an intelligent terminal pre-associated with the cryogenic physical therapy cabin;

the apparatus further comprises:

a reserved processing module, configured for before acquiring target feature information of a target user, adjusting the temperature of the cryogenic physical therapy cabin to reach the physical therapy temperature after determining that a current time reaches the reserved physical therapy time.

9. The apparatus according to claim 7, wherein the apparatus further comprises:

a second cabin door closing module, configured for, after adjusting the temperature of the cryogenic physical therapy cabin to a preset temperature, and controlling the cabin door of the cryogenic physical therapy cabin to be opened, controlling the cabin door of the cryogenic physical therapy cabin to be closed after determining that the user leaves the cryogenic physical therapy cabin.

10. The apparatus according to claim 7, wherein the apparatus further comprises:

a first acquisition module, configured for acquiring the temperature of the cryogenic physical therapy cabin and the physical therapy duration of the user;

a first control module, configured for increasing the temperature of the cryogenic physical therapy cabin, and/or controlling the cabin door of the cryogenic physical therapy cabin to be opened when it is determined that the temperature of the cryogenic physical therapy cabin is lower than a preset threshold, or when it is determined that the physical therapy duration of the user exceeds a preset duration.

11. The apparatus according to claim 7, wherein the apparatus further comprises:

a second acquisition module, configured for acquiring an emergency signal, wherein the emergency signal is a signal generated when a preset emergency button is triggered;

a second controlling module, configured for increasing the temperature of the cryogenic physical therapy cabin and/or controlling the cabin door of the cryogenic physical therapy cabin to be opened.

12. The apparatus according to claim 7, wherein the apparatus further comprises:

a device state acquisition module, configured for acquiring a device state of the cryogenic physical therapy cabin;

a prompt message sending module, configured for, when it is determined that an abnormal situation occurs in the cryogenic physical therapy cabin based on the device state of the cryogenic physical therapy cabin, sending a prompt message corresponding to the abnormal situation to a manufacturer of the cryogenic physical therapy cabin and/or a preset emergency contact.

13. An electronic device comprising a processor, a communication interface, a memory and a communication bus, wherein the processor, the communication interface and the memory communicate with each other via the communication bus;

the memory is configured for storing a computer program;

the processor is configured for executing a program stored in the memory to implement method steps of claim 1.

14. A non-transitory computer-readable storage medium, wherein a computer program is stored in the computer-readable storage medium, which, when executed by a processor, implements method steps of claim 1.

* * * * *